United States Patent [19]

Geldmacher

[11] 4,335,725
[45] Jun. 22, 1982

[54] THERAPEUTIC HEAT CUSHION

[76] Inventor: Barbara J. Geldmacher, Rte. 4, Box 736, Alvin, Tex. 77511

[21] Appl. No.: 178,511

[22] Filed: Aug. 15, 1980

[51] Int. Cl.$^3$ .............................................. A61F 7/00
[52] U.S. Cl. ...................................... 128/399; 219/527
[58] Field of Search ............... 128/399; 219/211, 212, 219/527, 52 B, 549

[56] References Cited

U.S. PATENT DOCUMENTS

| | | | |
|---|---|---|---|
| 2,429,583 | 10/1947 | Ogle | 219/211 |
| 2,712,592 | 7/1955 | Goldstein et al. | 219/528 |
| 3,013,141 | 12/1961 | Ellis | 219/528 |
| 3,017,493 | 1/1962 | Cooke | 219/528 |
| 3,103,219 | 9/1963 | Chaduer | 219/528 |
| 3,178,559 | 4/1965 | Fogel et al. | 128/399 |
| 3,480,760 | 11/1969 | Young | 219/528 |
| 4,044,221 | 8/1977 | Kuhn | 219/528 |

Primary Examiner—Robert W. Michell
Assistant Examiner—C. W. Shedd
Attorney, Agent, or Firm—Gunn, Lee & Jackson

[57] ABSTRACT

A novel portable cushion for selectively heating and supporting portions of a persons back while sitting or while riding in a car is disclosed, for therapeutic purposes and for comfort.

6 Claims, 3 Drawing Figures

THERAPEUTIC HEAT CUSHION

FIELD OF THE INVENTION

This invention relates generally to cushions for the heating of portions of a person's body. More particularly it relates to the heating and support of a persons lumbar area for therapeutic reasons and for comfort.

BACKGROUND OF THE INVENTION

The typical car seat is designed to support persons having a wide range of sizes and weights and as a result, the typical seat back is firm and cannot conform evenly to a person's anatomy. A person's buttocks and upper leg, being soft, can conform to a relatively firm seat but the average person's upper and lower back, being firm, connot conform to a firm back support. Therefore, to support a flexible heating member in conformity to the different size and shapes of peoples' backs, a means for the automatic and confortable position adjustment of the heating means is necessary for its practical use.

PRIOR ART

Ballard, U.S. Pat. No. 2,698,893, discloses a typical car seat having electrical circuitry for heating elements mounted within but having virtually no ability to conform to a person's back. Kuhn, U.S. Pat. No. 4,044,221 discloses a particular construction for a thin heated cover for a typical car seat. Cooke, U.S. Pat. No. 3,017,493, discloses a portable, flat, firm heating mat for heating a car seat. Goldstein, U.S. Pat. No. 2,712,592, discloses a hollow wire construction for use in a flat heating mat. Newton, U.S. Pat. No. 3,138,404, discloses "a rigid body of sheet material generally cup shaped". It is clear that none of the references above suggest or recognize the value of having a heating member conform to selected portions of a person's back so as to provide an even heat and pressure across the contact area, thereby eliminating hotspots, coldspots and serving as a back support to provide therapeutic action, to enhance comfort and to reduce or eliminate backache, particularly on long rides.

With regard to the lower back in particular, it has been found that a mild general heating of the lower back only can serve to reduce backache and improve the functioning of organs in the lumber area. The instant invention provides for the same service while riding in a car and in addition, can reduce muscle fatigue because the cushion can also act as support for the lumbar area against lateral motions induced by the movement of the car.

Therefore, it is a feature of the present invention to evenly and selectively heat a specific portion of a person's body while riding in a car.

It is also a feature of the present invention to evenly support a heating means against the lumbar area of a person's body.

It is another feature of the present invention to support the lumbar area of a person's body against lateral motions induced by the movement of the car.

It is still another feature of the present invention to reduce passenger fatigue resulting from a car ride.

It is another feature of the present invention to provide a therapeutic effect to cause better functioning and to relieve soreness of certain organs and muscles. Other advantages and features of the present invention will become obvious to those skilled in the art, and are within its spirit and scope.

SUMMARY OF THE PRESENT INVENTION

The present invention comprises portable means for holding a heating means in conformity with a selected portion of a person's back while the person is sitting in a chair or while riding in a car, so as to evenly and selectively heat that portion of the back and to provide lateral support against lateral motion induced by a persons weight or by movement of the car. The means comprises a heating wire mounted with or between glass fiber impregnated foil, or acrylic mesh panels or the like, positioned between a thick rear layer and a thin front layer of a soft heat transmissive material, all sealed within a moisture resistant cover of polyvinyl or the like, which in turn is enclosed by a removable and washable cover. The heating wire being insulated as is well known in the art, is disposed so as to provide evenly distributed heating against the portion of the body contacted by the cushion, and is connected to a suitable source of electricity such as an automobile cigarette lighter socket.

DESCRIPTION OF THE PREFERRED EMBODIMENT

Figure 1:
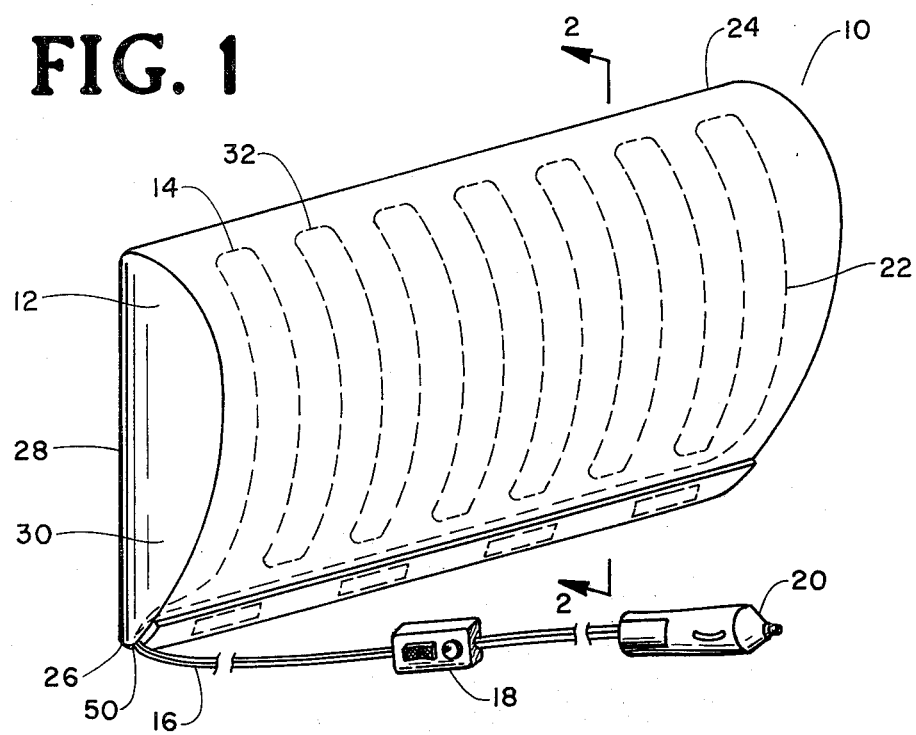
FIG. 1 illustrates an isometric view of the instant invention positioned as if to support the lumbar area of one's back.
Figure 3:
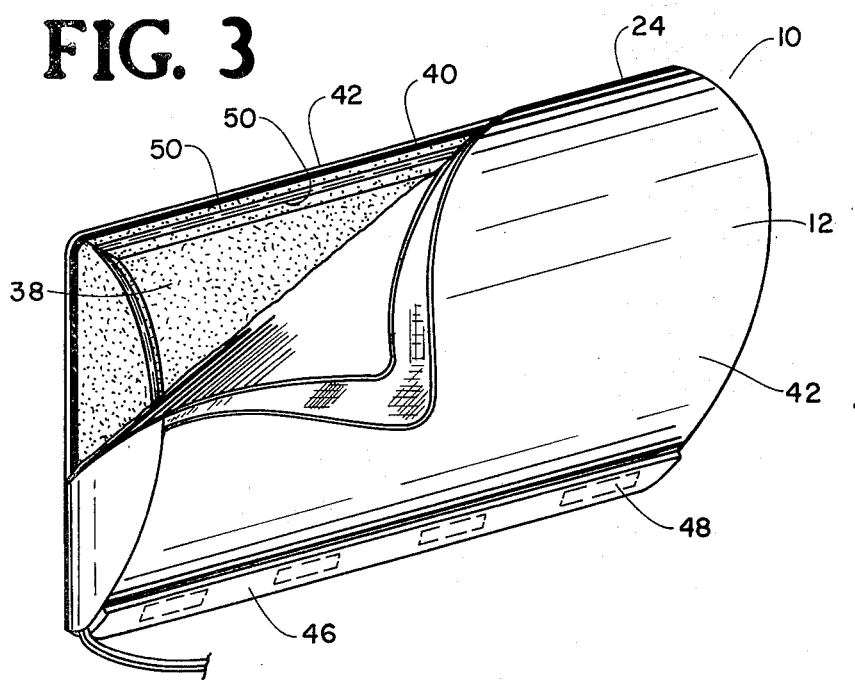
FIG. 3 is an isometric partially cut away view of the construction of the embodiment of the invention.

The invention is depicted in FIG. 1 generally as at 10, having composite cushion 12, containing heating wire 14 which is connected with electric cord 16 which in turn is connected through switch 18 and plug 20 to a suitable source of electricity such as an automobile cigarette lighter socket.

Figure 2:
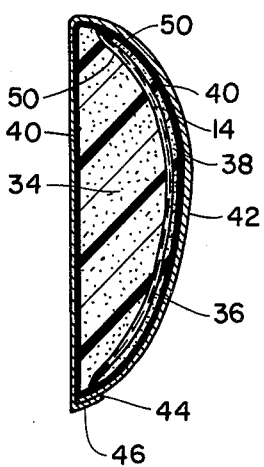
FIG. 2 is an enlarged vertical section taken along line 2—2 of FIG. 1.

Composite cushion 12 has arcuate surface 22 connected with the top edge 24 and bottom edge 26 of rear surface 28 and end surfaces as at 30 disposed between the sides of surfaces 22 and 28. As best seen in FIG. 2, the cushion 12 is of maximum depth, preferably 2½", at the approximate vertical mid point of the cushion, the depth decreasing as the top and bottom edges 24-26 are approached. The tapered contour of the cushion is thus optionally configured or placement in the lower back area for comforming to and support the lumbar region.

Heating wire 14 is located within and parallel to surface 22 so as to readily supply an even heating to surface 22, for instance, ⅜" below surface 22 and in a serpentine manner preferably comprising 10 to 14 loops as illustrated by dotted lines in FIG. 1 as at 32. The heating wire 14 is preferably sandwiched between two glass fiber impregnated foil panels 50 which carry and securely locate the heating wire. As best shown in FIG. 2, composite cushion 12 comprises: soft resilient member 34 made of such material as a urethane foam and being relatively thick as compared to other members of the composite cushion for instance 2⅛" thick, heating wire 14 mounted with flexible panel 36 formed by the foil panels 50, wire 14 being disposed as shown by dotted lines 32 in FIG. 1; pad 38 made of a soft, heat transmissive material suitable or use as a heating pad, preferably a urethane foam one quarter inch thick, or the like;

moisture resistant cover 40 made of polyvinyl or the like, cover 40 being sealed around members 14, 34, 36 and 38 so as to exclude moisture due to factors such as presperation, humidity, drink spills or such; outer cover 42 which encloses cover 40, cover 42 having an opening 44 along bottom edge 26 for both installation and removal of cover 40 together with members therein for the purpose of being able to wash or otherwise clean cover 42, opening 44 having closure means as by flap or seam 46 held closed by conventional snaps 48.

Within moisture resistant cover 40, heating wire 14 is connected to conventional insulated electric cord 16, cover 40 also sealing around wire 16 as at opening 50 through which wire 16 extends through cover 40.

Switch 18 may be of the off-on type or may provide conventional high-low controls or indeed may be a conventional rheostat-switch so as to provide stepless heat control.

OPERATION OF THE INVENTION

When the user desires a therapeutic effect across the back while driving in an automobile, cushion 12 is suitably positioned against the back of the car seat such as by resting lower edge 26 on the seat, so as to heat and to cushion the desired portion of the back. Plug 20 is then connected to the source of electricity. After the user assumes position on the seat, the user leans back into the cushion, causing the cushion to conform to the desired portion of the back and thereby position the heating wire evenly disposed from that portion of the back so as to deliver an even heating effect and substantially an even support pressure. Thereafter, switch 18 may be manipulated by the user to adjust the heating effect as desired.

It is therefore clear that the present invention provides a novel means for the even support of a selective heating means for use on selected portions of a person's back while sitting or while riding in a car for therapeutic reasons and for comfort.

What is claimed is:

1. A portable unitary therapeutic heat supplying cushion adapted for use by a person in the seated position, said cushion comprising:
   (a) a soft, resilient internal member having a back surface of substantially planar form for contact with the back portion of the seat or chair within which the person sits, said resilient member further having a curved front surface generally conforming to the lower back or lumbar area of the human body,
   (b) a pair of panels conforming to the curvature of said front surface of said internal member;
   (c) electrical heating means interposed between said pair of panels;
   (d) a heat transmissive pad, of less thickness as compared to the thickness of said resilient member, covering the outer one of said pair of panels and conforming to the curvature thereof;
   (e) a moisture resistant enclosure enclosing said resilient internal member, panels, electrical heating means and heat transmissive pad;
   (f) a protective cover enclosing said moisture resistant closure and the contents thereof said protective cover being removable for cleaning; and
   (g) a selectively controllable electrical heating circuit being connectable to a source of electrical energy and being operatively coupled to said electrical heating means.

2. The invention of claim 1 wherein said heating means comprises an electrical heating wire arranged in serpentine manner between said panels.

3. The invention of claim 1 wherein said resilient member and said heat transmissive pad are composed of plastic foam.

4. The invention of claim 1, wherein:
   said electrical heating circuit is adapted for connection to direct electrical current and incorporates heat control means enabling the user to select the desired heat developed by said heating means.

5. The invention of claim 1, wherein:
   said pair of panels are composed of glass fiber impregnated foil.

6. The invention of claim 1, wherein:
   (a) said protective cover defines an opening along one side thereof for insertion and removal of said heat supplying cushion; and
   (b) closure means being provided on said protective cover to ensure retention of said cushion therein.

* * * * *